United States Patent
Cunningham et al.

(10) Patent No.: US 7,497,992 B2
(45) Date of Patent: Mar. 3, 2009

(54) DETECTION OF BIOCHEMICAL INTERACTIONS ON A BIOSENSOR USING TUNABLE FILTERS AND TUNABLE LASERS

(75) Inventors: Brian T. Cunningham, Lexington, MA (US); Peter Y. Li, Andover, MA (US); Constance Chang-Hasnain, Palo Alto, CA (US); Carlos Mateus, Albany, CA (US)

(73) Assignees: SRU Biosystems, Inc., Woburn, MA (US); The Regents of the University of California, Oakland, CA (US)

( * ) Notice: Subject to any disclaimer, the term of this patent is extended or adjusted under 35 U.S.C. 154(b) by 939 days.

(21) Appl. No.: 10/434,015

(22) Filed: May 8, 2003

(65) Prior Publication Data

US 2004/0223881 A1    Nov. 11, 2004

(51) Int. Cl.
*C12M 1/34* (2006.01)
*C12M 3/00* (2006.01)
*G01N 33/53* (2006.01)
*G01N 21/00* (2006.01)

(52) U.S. Cl. .................... 422/82.05; 422/82.11; 435/6; 435/7.1; 435/283.1; 435/287.1; 435/287.2; 250/227.23; 250/227.27; 250/227.28; 436/164

(58) Field of Classification Search .................. 385/12; 370/20; 422/82.11; 356/326
See application file for complete search history.

(56) References Cited

U.S. PATENT DOCUMENTS 4,009,933 A    3/1977    Firester ...................... 350/152

(Continued)

FOREIGN PATENT DOCUMENTS

EP    0112721    7/1987

(Continued)

OTHER PUBLICATIONS

Garnache et al., "High-Sensitivity Intracavity Laser Absorption Spectroscopy with Vertical-External-Cavity Surface-Emitting Semiconductor Lasers" Optics Letters, Optical Society of America, vol. 24, No. 12, pp. 826-828 (Jun. 15, 1999).

(Continued)

*Primary Examiner*—Jill Warden
*Assistant Examiner*—Neil Turk
(74) *Attorney, Agent, or Firm*—McDonnell Boehnen Hulbert & Berghoff LLP

(57) ABSTRACT

An apparatus and method for detection of peak wavelength values of colorimetric resonant optical biosensors using tunable filters and tunable lasers is provided. Biomolecular interactions may be detected on a biosensor by directing collimated white light towards a surface of the biosensor. Molecular binding on the surface of the biosensor is indicated by a shift in the peak wavelength value of reflected or transmitted light from the biosensor, while an increase in the wavelength corresponds to an increase in molecular absorption. A tunable laser light source may generate the collimated white light and a tunable filter may receive the reflected or transmitted light and pass the light to a photodiode sensor. The photodiode sensor then quantifies an amount of the light reflected or transmitted through the tunable filter as a function of the tuning voltage of the tunable filter.

20 Claims, 11 Drawing Sheets

U.S. PATENT DOCUMENTS

| | | | |
|---|---|---|---|
| 4,536,608 A | 8/1985 | Sheng et al. | 136/259 |
| 4,576,850 A | 3/1986 | Martens | 428/156 |
| 4,668,558 A | 5/1987 | Barber | 428/156 |
| 4,876,208 A | 10/1989 | Gustafson et al. | |
| 4,931,384 A | 6/1990 | Layton et al. | 435/7 |
| 4,992,385 A | 2/1991 | Godfrey | |
| 4,999,234 A | 3/1991 | Cowan | 428/156 |
| 5,118,608 A | 6/1992 | Layton et al. | 435/7.1 |
| 5,175,030 A | 12/1992 | Lu et al. | 428/30 |
| 5,229,614 A | 7/1993 | Andersson et al. | 250/370.12 |
| 5,268,782 A | 12/1993 | Wenz et al. | 359/81 |
| 5,413,884 A | 5/1995 | Koch et al. | 430/5 |
| 5,442,169 A | 8/1995 | Kunz | 250/227.21 |
| 5,455,178 A | 10/1995 | Fattinger | |
| 5,478,527 A | 12/1995 | Gustafson et al. | |
| 5,478,756 A | 12/1995 | Gizeli et al. | 436/527 |
| 5,492,840 A | 2/1996 | Malmqvist et al. | |
| 5,496,701 A | 3/1996 | Pollard-Knight | 435/7.4 |
| 5,500,188 A * | 3/1996 | Hafeman et al. | 204/403.01 |
| 5,559,338 A | 9/1996 | Elliott et al. | 250/492.1 |
| 5,580,784 A * | 12/1996 | Berndt | 435/288.7 |
| 5,598,267 A | 1/1997 | Sambles et al. | 356/369 |
| 5,598,300 A | 1/1997 | Magnusson et al. | 359/566 |
| 5,615,052 A | 3/1997 | Doggett | 359/811 |
| 5,629,951 A * | 5/1997 | Chang-Hasnain et al. | 372/20 |
| 5,690,894 A | 11/1997 | Pinkel et al. | 422/68.1 |
| 5,691,846 A | 11/1997 | Benson, Jr. et al. | 359/530 |
| 5,732,173 A | 3/1998 | Bylander et al. | 385/49 |
| 5,738,825 A | 4/1998 | Rudigier et al. | 422/82.11 |
| 5,771,328 A | 6/1998 | Wortman et al. | 385/146 |
| 5,792,411 A | 8/1998 | Morris et al. | 264/400 |
| 5,804,453 A | 9/1998 | Chen | 436/518 |
| 5,846,843 A | 12/1998 | Simon | 436/527 |
| 5,925,878 A | 7/1999 | Challener | 250/225 |
| 5,955,378 A | 9/1999 | Challener | 436/525 |
| 5,986,762 A | 11/1999 | Challener | 356/375 |
| 5,991,480 A | 11/1999 | Kunz et al. | 385/37 |
| 5,994,150 A | 11/1999 | Challener et al. | 436/518 |
| 6,035,089 A | 3/2000 | Grann et al. | 385/129 |
| 6,076,248 A | 6/2000 | Hoopman et al. | 29/527.1 |
| 6,088,505 A | 7/2000 | Hobbs | 385/147 |
| 6,091,504 A | 7/2000 | Walker et al. | 356/437 |
| 6,100,991 A | 8/2000 | Challener | 356/445 |
| 6,146,593 A | 11/2000 | Pinkel et al. | 422/68.1 |
| 6,154,591 A * | 11/2000 | Kershaw | 385/39 |
| 6,185,019 B1 | 2/2001 | Hobbs et al. | 359/30 |
| 6,320,991 B1 | 11/2001 | Challener et al. | 385/12 |
| RE37,473 E | 12/2001 | Challener | 250/225 |
| 6,338,968 B1 | 1/2002 | Hefti | 436/518 |
| 6,340,598 B1 | 1/2002 | Herron et al. | 436/518 |
| 6,346,376 B1 | 2/2002 | Sigrist et al. | 435/5 |
| 6,474,164 B1* | 11/2002 | Mucciardi et al. | 73/602 |
| 6,549,687 B1* | 4/2003 | Kochergin et al. | 385/12 |
| 6,965,431 B2* | 11/2005 | Vo-Dinh et al. | 356/301 |
| 2002/0018610 A1 | 2/2002 | Challener et al. | 385/12 |
| 2005/0070027 A1* | 3/2005 | Gollier et al. | 436/518 |
| 2006/0193550 A1 | 8/2006 | Wawro et al. | 385/12 |

FOREIGN PATENT DOCUMENTS

| | | |
|---|---|---|
| EP | 0517777 | 12/1992 |
| EP | 0660924 | 7/1995 |
| GB | 2227089 | 7/1990 |
| WO | 8402578 | 7/1984 |
| WO | 9008318 | 7/1990 |
| WO | 9113339 | 9/1991 |
| WO | 9221768 | 12/1992 |
| WO | 9314392 | 7/1993 |
| WO | 9503538 | 2/1995 |
| WO | 9857200 | 12/1998 |
| WO | 9909392 | 2/1999 |
| WO | 9909396 | 2/1999 |
| WO | WO9957789 | 11/1999 |
| WO | 9966330 | 12/1999 |
| WO | 0023793 | 4/2000 |
| WO | 0104697 | 1/2001 |

OTHER PUBLICATIONS

Cullum et al. "Development of a Portable Raman Spectrometer for Medical Diagnostics", Proceedings of the SPIE, vol. 4615, pp. 82-90 (2002).

PCT International Search Report and Written Opinion for PCT application No. PCT/US2004/014262, application of SRU Biosystems, Inc., dated Nov. 2, 2004.

International Preliminary Report on Patentability in PCT/US2004/014262, dated Jul. 4, 2005.

Cowan, "The Recording and Large Scale Replication of Crossed Holographic Grating Arrays using Multiple Beam Interferometry", SPIE, vol. 503, *Application, Theory, and Fabrication of Periodic Structures*, pp. 120-129 (1984).

Cowan, "Holographic honeycomb microlens", vol. 24, No. 5, *Optical Engineering*, pp. 796-802 (1985).

Cowan, et al., "The Recording and Replication of Holographic Micropatterns for the Ordering of Photographic Emulsion Grains in Film Systems", vol. 31, No. 3, *J. Imaging Sci.*, pp. 100-107 (1987).

Wang, et al., "Guided-mode Resonances in Planar Dielectric-Layer Diffraction Gratings", vol. 7, No. 8, *J. Opt. Soc. Am.*, pp. 1470-1474 (1990).

Cowan, "Aztec Surface-Relief Volume Diffractive Strucutre", vol. 7, No. 8, *J. Opt. Soc. Am.*, pp. 1529-1544 (1990).

Patel, et al., "Multiwavelength Tunable Liquid-Crystal Etalon Filter", vol. 3, No. 7, *IEEE Photonics Technology Letters*, pp. 643+-644 (1991).

Patel, et al., "Electrically Tunable and Polarization Insensitive Fabry-Perot etalon with a Liquid-Crystal Film", vol. 58, No. 22, *American Institute of Physics*, pp. 2491-2493 (1991).

Magnusson, et al., "*New Principle for Optical Filters*", Appl. Phys. Lett., vol. 61, No. (9), Aug. 31, 1992 pp. 1022-1024.

Wang, et al., "Theory and Applications of Guided-Mode Resonance Filters", vol. 32, No. 14, *Applied Optics*, pp. 2606-2613 (1993).

Wang, et al., "Design of Waveguide-Grating Filters with Symmetrical Line Shapes and Low Sidebands", vol. 19, No. 12, *Optical Society of America*, pp. 919-921 (1994).

Jin, et al., "A Biosensor Concept Based on Imaging Ellipsometry for Visualization of Biomolecular Interactions", 232, *Analytical Biochemistry*, p. 69-72 (1995).

Brecht, et al., "Optical Probes and Transducers", vol. 10, *Biosensors & Bioelectronics*, pp. 923-936 (1995).

Magnusson, et al., "Transmission Bandpass Guided-Mode Resonance Filters", vol. 34, No. 35, *Applied Optics*, pp. 8106-8109 (1995).

Peng, et al., "Experiemental Demonstration of Resonant Anomalies in Diffraction from Two-Dimensional Gratings", vol. 21, No. 8, *Optics Letters*, pp. 549-551 (1996).

Sigal, et al., "A Self-Assembled Monolayer for the Binding and Study of Histidine-Tagged Proteins by Surface Plasmon Resonance", vol. 68, No. 3, *Analytical Chemistry*, pp. 490-497 (1996).

Peng, et al., "Resonant Scattering from Two-Dimensional Gratings", vol. 13, No. 5, *J. Opt. Soc. Am. A.*, pp. 993-1005 (1996).

Jordan, et al., "Surface Plasmon Resonance Imaging Measurements of Electrostatic Biopolymer Adsorption onto Chemically Modified Gold Surfaces", vol. 69, No. 7, *Analytical Chemistry*, pp. 1449-1456 (1997).

Raguin, et al., "Structured Surfaces Mimic Coating Performance", *Laser Focus World*, pp. 113-117 (1997).

Lin, et al., "A Porous Silicon-Based Optical Interferometric Biosensor", vol. 278, *Science*, pp. 840-843 (1997).

Morhard, et al., Immobilization of Antibodies in Micropatterns for Cell Detection by Optical Diffraction, *Sensors and Actuators B 70*, pp. 232-242 (2000).

Jenison, et al., "Interference-Based Detection of Nucleic Acid Targets on Optically Coated Silicon", vol. 19, *Nature Biotechnology*, pp. 62-64 (2001).

Cunningham, et al., U.S. Provisional Patent Application, *"Resonant Reflection Microarray"*, U.S. Appl. No. 60/244,312, filed Oct. 30, 2000.

Cunningham, et al., U.S. Provisional Patent Application, *"Resonant Reflection Microarray"*, U.S. Appl. No. 60/283,314, filed Apr. 12, 2001.

Cunningham, et al., U.S. Provisional Patent Application, *"Resonant Reflection Microarray"*, U.S. Appl. No. 60/303,028, filed Jul. 3, 2001.

Challener, et al., "A Multiplayer Grating-Based Evanescent Wave Sensing Technique", *Elsevier Science B.B.*, pp. 42-46 (2000).

Huber, et al., "Direct Optical Immunosensing (Sensitivity and Selectivity)", *Sensors and Actuators B*, 6, pp. 122-126 (1992).

Invitation to Pay Additional Fees in foreign counterpart application PCT/US01/50723.

Hobbs, et al., "Automated Interference Lithography Systems for Generation of Sub-Micron Feature Size Patterns", *SPIE*, vol. 3879, pp. 124-135, Sep. 1999.

Cunningham, et al., *"Introduction to Bioanalytical Sensors"*, *Techniques in Analytical Chemistry*, pp. 260-291, 1998.

International Search Report for foreign counterpart application PCT/US01/50723.

Cunningham, et al, U.S. Patent Application, *"Label-Free High-Throughput Optical Technique for Detecting Biomolecular Interactions"* U.S. Appl. No. 09/930,352, filed Aug. 15, 2001; Publication No. 0127565-A1; published Sep. 12, 2002.

Cunningham, et al, U.S. Patent Application, *"Resonant Reflection Microarray"* Serial No. 01/45455; filed Oct. 23, 2001; Publication No. 02/061429, published Aug. 8, 2002.

Cunningham, et al, U.S. Patent Application, *"Guided Mode Resonant Filter Biosensor Using a Linear Grating Surface Structure"* U.S. Appl. No. 10/059,060, filed Jan. 28, 2002; Publication No. 0027328-A1, published Feb. 6, 2003.

Cunningham, et al, U.S. Patent Application, *"Optical Detection of Label-Free Biomolecular Interactions Using Microreplicated Plastic Sensor Elements"* U.S. Appl. No. 10/058,626, filed Jan. 28, 2002; Publication No. 0027327-A1, published Feb. 6, 2003.

Pandey, A. and Mann, M. *"Proteomics to Study Genes and Genomes"* Nature. Jun. 15, 2000;405(6788):837-46.

Patterson, S.D. *"Proteomics: the Industrialization of Protein Chemistry"* Current Opinions in Biotechnology. Aug. 2000;11(4):413-8.

Cunningham, B. et al., *"A Plastic Colormetric Resonant Optical Biosensor for Multiparallel Detection of Label-Free Biochemical Interactions"* Sensors and Actuators B 85; pp. 219-226 (2002).

Cunningham, B. et al., *"Colorimetric Resonant Reflection as a Direct Biochemical Assay Technique"* Sensors and Actuators B 81; pp. 316-328 (2002).

International Search Report for foreign counterpart application PCT/US03/01175.

Chang-Hasnain, C.J., *"Tunable VCSEL"* IEEE Journal on Selected Topics in Quantum Electronics., vol. 6 No. 6, pp. 978-987, Nov./Dec. (2000).

Li, G.S., Yuen, W., and Chang Hasnain, C.J., *"Wide and Continuously Tunable (30nm)Detector with Uniform Characteristics Over Tuning Range"* Electronics Letters, Jun. 19, 1997, vol. 33 No. 13, pp. 1122-1123.

Mateus, C.F.R., Chang, C., Chrostowski, L., Yang, S., Sun, D., Pathak, R., Chang-Hasnain, C.J., *"Widely Tunable Torsional Optical Filter"* IEEE Photonics Technology Letters, vol. 14, No. 6, pp. 819-821, Jun. 2002.

\* cited by examiner

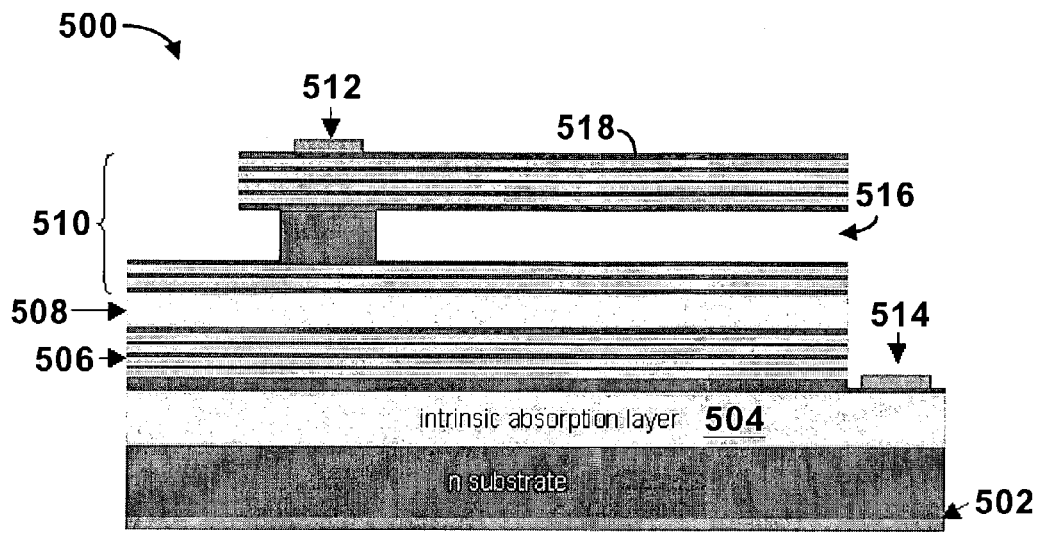
FIGURE 5A
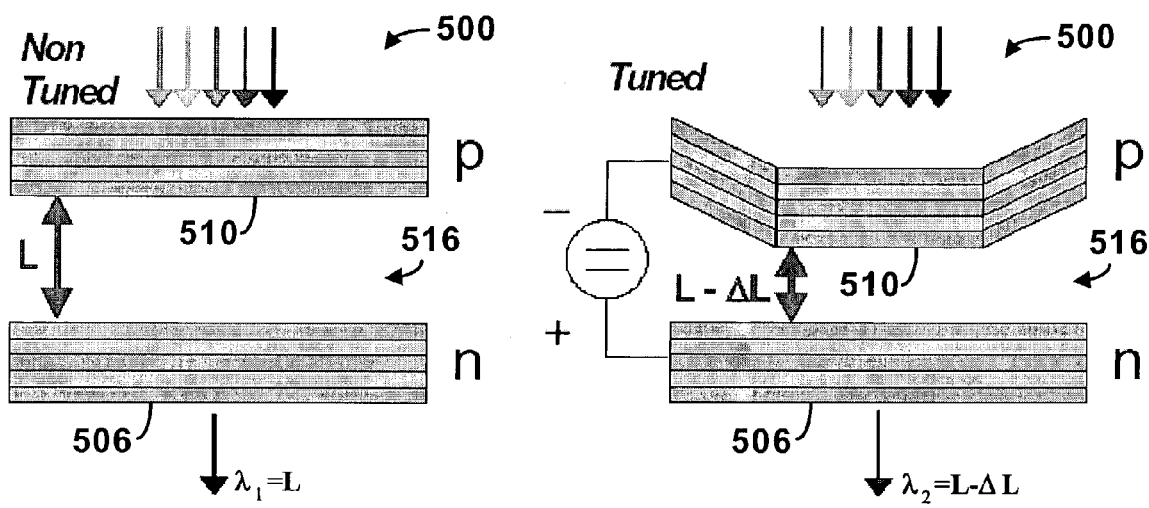
FIGURE 5B   FIGURE 5C

DETECTION OF BIOCHEMICAL INTERACTIONS ON A BIOSENSOR USING TUNABLE FILTERS AND TUNABLE LASERS

FIELD OF INVENTION

The present invention generally relates to a method and system for detecting biomolecular interactions, and more particularly to the detection of calorimetric resonant optical biosensor peak wavelength values using tunable filters and tunable lasers.

BACKGROUND

There have recently been rapid advances in molecular biology. For example, one significant accomplishment was the completion of the sequencing of the human genome. Presently, another challenge is to understand how the many protein targets encoded by the DNA interact with other proteins, small molecule pharmaceutical candidates, and a large host of enzymes and inhibitors.

To determine such interactions, assays may be completed using biosensors. Biosensors have been developed to detect a variety of biomolecular interactions including antibody-antigen, hormone-receptor, and enzyme-substrate interactions. Biosensors include a highly specific recognition element and a transducer that converts a molecular recognition event into a quantifiable signal. Signal transduction has been accomplished by many methods including fluorescence, interferometry, and gravimetry, for example.

For the majority of assays for genomics, proteomics, pharmaceutical compound screening, and clinical diagnostic applications completed using biosensors, fluorescent or calorimetric chemical labels are commonly attached to the molecules under study so these molecules may be readily visualized. However, attachment of a label substantially increases assay complexity and possibly alters functionality of the molecules through conformational modification or epitope blocking.

Detection of biomolecular interactions may be accomplished using label free detection techniques. For example, label free detection techniques include measuring changes in mass, changes in microwave transmission line characteristics, microcantilever deflection, or optical density detection.

Unfortunately, however, the widespread commercial acceptance of label free biosensor technologies has been limited by the lack of ability to provide high detection sensitivity in a format that is inexpensive to manufacture and package. For example, label free detection biosensors fabricated upon semiconductor or glass wafers are costly to produce and package if the sensor area is large enough to contain a number of parallel assays. Similarly, providing for electrical connections to individual biosensors in an array of biosensors poses difficult challenges in packaging, and compatibility with fluid exposure. In addition, many label free biosensor transduction methods (e.g., surface plasmon resonance ("SPR"), output grating coupling, ellipsometry, evanescent wave detection, and reflectance interference spectroscopy ("RIS")) are rather slow and can be very expensive. Furthermore, some of these label free detection methods are limited to dry samples, and thus are not suited for samples immersed in fluid. This substantially limits applications for these biosensors.

As the industry evolves from the detection of genes towards identification of protein interactions for example, the emphasis shifts from simply identifying structure to identifying both structure and function. Also, there are many more proteins than genes, which increases difficulty in the identification process. Indeed, the use of labels, such as colorimetric or fluorescent tags, for genomic investigations is known to adversely affect the structure and function of some proteins. In addition, the limitations of existing label free technologies present too many obstacles to overcome. Therefore, there is a need for a new sensing mechanism that can monitor assays without the use of labels, is amenable to ultra high throughput, and can lower the cost per assay performed.

SUMMARY

In an exemplary embodiment of the present invention, a measuring apparatus for detecting a biochemical interaction on a biosensor is provided. The measuring apparatus comprises a light source that generates collimated white light and directs the collimated white light towards a surface of the biosensor. The apparatus also includes a tunable filter that receives light transmitted through the biosensor and passes a narrow band of light that has wavelengths substantially centered at a passband wavelength and reflects substantially all other wavelengths. The passband wavelength may be adjusted according to a tuning voltage of the tunable filter.

In another embodiment, the measuring apparatus includes a tunable laser light source and a photodiode detector. The tunable laser light source generates light that has a tunable laser wavelength and directs the light towards a surface of the biosensor. The tunable laser wavelength is tuned by adjusting a tuning voltage. The photodiode detector receives light transmitted through the biosensor and detects a broad band of wavelengths encompassing a wavelength passband. An output of the photodiode detector quantifies an amount of the light transmitted through the biosensor as a function of the tuning voltage.

In still another embodiment, an apparatus for detecting a maximum wavelength of reflected light is provided. The apparatus comprises a light source that generates collimated white light and a power splitter that directs the collimated white light towards a surface of a sensor. The apparatus further comprises a tunable detector that receives light reflected by the sensor and measures a radiation spectrum of the light reflected from the sensor. The tunable detector filters a narrow band of light that has wavelengths substantially centered at a passband wavelength from the light reflected by the sensor and this passband wavelength is adjusted according to a tuning voltage of the tunable detector.

In yet another embodiment, the apparatus for detecting a maximum wavelength of reflected light comprises a tunable laser light source, an optical circulator, and a photodiode detector. The tunable laser light source generates a tunable single wavelength of light and can be tuned by adjusting a tuning voltage. The optical circulator directs the tunable single wavelength of light towards a surface of a sensor. In turn, the photodiode detector receives light reflected from the biosensor and detects a broad band of wavelengths encompassing a wavelength passband. An output of the photodiode detector quantifies an amount of the light reflected from the biosensor as a function of the tuning voltage.

These as well as other features and advantages will become apparent to those of ordinary skill in the art by reading the following detailed description, with appropriate reference to the accompanying drawings.

BRIEF DESCRIPTION OF FIGURES

Exemplary embodiments of the present invention are described herein with reference to the drawings, in which:

FIG. 5A illustrates another embodiment of a tunable detector;

FIGS. 5B and 5C are schematic diagrams illustrating one embodiment of tuning the tunable detector of FIG. 5A;

DETAILED DESCRIPTION OF EXEMPLARY EMBODIMENTS

The present invention generally relates to a method and system for detecting biomolecular interactions. These biomolecular interactions may occur on a surface of a biosensor. In one embodiment, the biosensor is a colorimetric resonant optical biosensor embedded into a surface of a microarray slide, microtiter plate or other device.

The colorimetric resonant optical biosensor allows biochemical interactions to be measured on the sensor's surface without the use of fluorescent tags or colorimetric labels. Thus, the colorimetric resonant optical biosensor provides for label free detection of these interactions. For more information concerning label-free detection, reference is made to the following commonly owned U.S. Patent Applications, which are all fully incorporated herein by reference: "Method And Instrument For Detecting Biomolecular Interactions," as described in U.S. patent application Ser. No. 10/180,374, filed on Jun. 26, 2002; "Method And Apparatus For Detecting Biomolecular Interactions," as described in U.S. patent application Ser. No. 10/180,647, filed on Jun. 26, 2002; and "Label-Free Methods For Performing Assays Using A Colorimetric Resonant Optical Biosensor," as described in U.S. patent application Ser. No. 10/237,641, filed on Sep. 9, 2002.

Generally, to detect a biochemical interaction on a biosensor, an optical structure on a surface of the calorimetric resonant optical biosensor is illuminated with collimated white light. The optical structure is designed to reflect only a narrow band of wavelengths, which is described as a wavelength "peak." The peak wavelength value ("PWV") changes when biological material is deposited or removed from the biosensor surface.

According to an exemplary embodiment of the present invention, a tunable laser may illuminate the biosensor. Biochemical interactions may then be detected using a tunable detector or a tunable filter. A spectrum interpretation can then be transduced to a dynamic protein characteristic that is attached to the biosensor.

Figure 1:
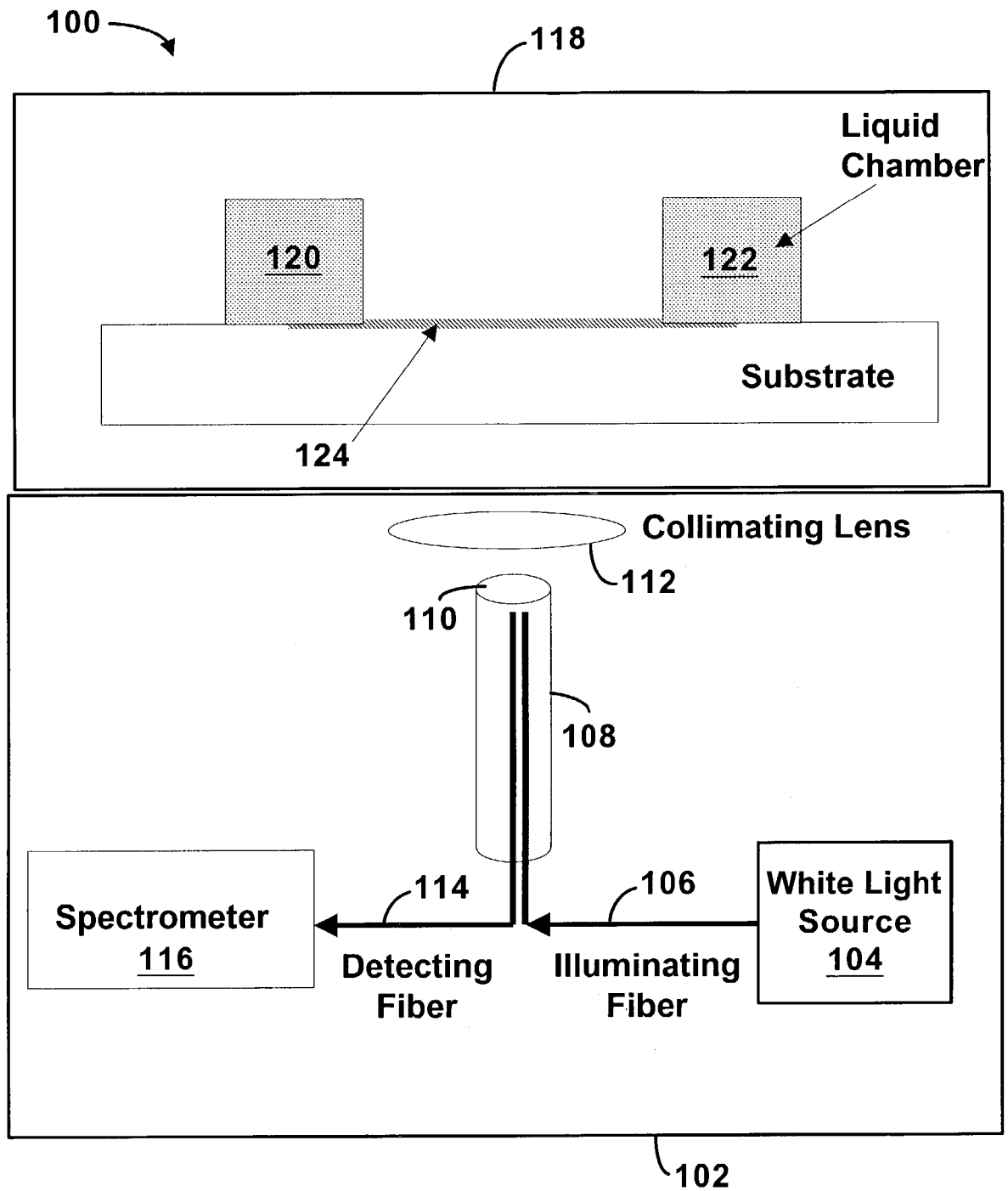
FIG. 1 illustrates a basic diagram of one embodiment of an optical device.

Referring now to the figures, FIG. 1 illustrates one embodiment of an optical device 100 that comprises an optical fiber probe measuring apparatus 102 and a biosensor 118. It should be understood that this and other arrangements described herein are set forth for purposes of example only, and other arrangements and elements can be used instead and some elements may be omitted altogether, for example. In addition, arrangements described herein may be used for multiple applications. For example, in one application, biosensor 118 can be incubated in a incubation enclosure and moved to a position for reading. Incubation may occur at a user determined temperature. In another application, an instrument incorporating measuring apparatus 102 may also provide a mechanism for mixing samples within a microtiter plate well while the optical sensor resides inside the apparatus. The mixing could take the form of a shaking mechanism or other type of system. Other examples are possible as well.

FIG. 1 illustrates a basic design for a PWV detector that can be adapted to a variety of possible instrumentation configurations. Measuring apparatus 102 includes a white light source 104 coupled via an illuminating fiber 106 to an optical fiber probe 108, which includes a detection head 110. A collimating lens 112 is positioned over optical fiber probe 108. In turn, optical fiber probe 108 is coupled via a detecting fiber 114 to a spectrometer 116. Biosensor 118 is positioned above collimating lens 112. A test sample is placed on biosensor 118 in the space between structures 120 and 122 for binding to receptors on a surface 124. Measuring apparatus 102 measures biochemical interactions occurring on surface 124 of biosensor 118 without the use of fluorescent tags or calorimetric labels. Optical device 100 may have the characteristics of the biosensor devices as herein previously described, such as a well of microtiter plate. For example, biosensor 118 may be embedded within a bottom portion of a conventional microtiter plate.

Illuminating fiber 106 directs an area of collimated light, via the collimating lens 112, on surface 124, which is preferably a bottom surface of biosensor 118. Illuminating fiber 106 is bundled along with detecting fiber 114 in a unitary optical fiber probe. Detecting fiber 114 is utilized to collect light reflected from biosensor 118. Detecting fiber 114 channels the reflected light to spectrometer 116, which is preferably a wavelength spectrometer. Spectrometer 116 processes the reflected light to determine characteristics of the reflected light.

In particular, measuring apparatus 102 collects light reflected from the illuminated biosensor surface 124 and scans detection head 10 across the biosensor surface. White light source 104, for example, illuminates about a ~1 millimeter (mm) diameter region of surface 124 through about a 400 micrometer (μm) diameter fiber optic and collimating lens 112 at nominally normal incidence through the bottom of a microtiter plate, for example. Such a microtiter plate could have a standard 96-well, 384-well, or 1526-well microtiter plate format, but with a biosensor attached to the bottom, for example.

When surface 124 is illuminated with collimated white light generated by white light source 104, surface 124 reflects only a narrow band of wavelengths. This narrow band of wavelengths is referred to as a wavelength peak. The "peak wavelength value" (PWV) changes when biological material is deposited or removed from surface 124. That is, the PWV changes when a biological material is deposited between structures 120 and 122. Based on light reflected off surface 124, measuring apparatus 102 can measure certain values, such as the PWV's of a plurality of locations within biosensor 118. Collected reflected light is gathered into spectrometer 116 for processing. For example, spectrometer may then generate a PWV for the biosensor 118.

Optical device 100 provides for determining the PWV of a colorimetric resonant optical biosensor by simultaneous illumination of a biosensor at normal incidence with a broad band of wavelengths, and simultaneous detection of a broad band of reflected or transmitted wavelengths. The illuminating light should be substantially collimated (e.g., parallel) in order to produce a narrow resonance band on the reflected or transmitted radiation spectrum. The illuminating radiation can be provided by a white light source, such as a light bulb, or a light emitting diode (LED) with a radiating spectrum that encompasses the resonance wavelength, for example.

When a resonance wavelength is within the band of illuminating wavelengths, a high reflected intensity (or low transmitted intensity) is obtained only at the resonance wavelength. When the reflected (or transmitted) light is gathered into a spectrometer that accepts light in a range of wavelengths containing the resonance wavelength, the spectrometer can measure the reflected (or transmitted) intensity as a function of wavelength. The extent of the shift of reflected wavelength can be used to determine an amount of bound molecules in the sample and the chemical affinity between receptor molecules and an analyte. For example, when molecules are attached to the surface of the biosensor, the reflected wavelength is shifted due to the change of the optical path of light within the grating. Consequently, by linking receptor molecules to the grating surface, complimentary binding molecules (e.g., analytes) can be detected without the use of any kind of fluorescent probe or particle label.

In one embodiment, biosensor 118, when illuminated with white light, is designed to reflect only a single wavelength. Subwavelength structured surfaces (SWS) are generally an unconventional type of diffractive optic that can mimic the effect of thin-film coatings. These structures may be used as antireflection filters, polarizing filters, and narrowband filters. See, e.g. S. Peng and G. M. Morris, "Resonant scattering from two-dimensional gratings," *J. Opt. Soc. Am. A*, Vol. 13, No. 5, p. 993, May 1996; R. Magnusson, and S. S. Want, "New principle for optical filters," *Appl. Phys. Lett.*, 61, No. 9, p. 1022, August, 1992; and S. Peng and G. Morris, "Experimental demonstration of resonant anomalies in diffraction from two-dimensional gratings," *Optics Letters*, Vol. 21, No. 8, p. 549, April, 1996, the full disclosures of which are herein incorporated by reference.

An SWS structure contains a surface-relief grating in which the grating period is small compared to the wavelength of incident light. In this manner, no diffractive orders other than the reflected and transmitted zeroth orders are allowed to propagate. To design a SWS surface narrowband filter, a two-dimensional grating is sandwiched between a substrate and a cover layer that fills the grating grooves. When the effective index of refraction of the grating region is greater than the substrate or the cover, a waveguide-like region is created. When the filter is designed properly, incident light passes into the waveguide region and propagates as a leaky mode. The grating structure selectively couples light at a narrow band of wavelengths into a mode that can travel laterally across the grating surface. The light propagates only a short distance (on the order of 10-100 micrometers), undergoes scattering, and couples with the forward- and backward-propagating zeroth-order light. This sensitive coupling condition can produce the resonant grating effect on the reflected radiation spectrum, resulting in a narrow band of reflected or transmitted wavelengths.

When specific binding substances are attached to the surface of biosensor 118, the reflected wavelength (e.g., color) is shifted due to the change of the optical path of light that is coupled into the grating. By linking specific binding substances to a biosensor surface, complementary binding partner molecules can be detected without the use of any kind of fluorescent probe or particle label. The detection technique is capable of resolving changes of, for example, ~0.1 nanometer (nm) thickness of protein binding, and can be performed with the biosensor surface either immersed in fluid or dried. A more detailed description of these binding partners is provided in related and commonly assigned U.S. patent application Ser. No. 09/930,352, entitled "Label-Free High-Throughput Optical Technique For Detecting Biomolecular Interactions," filed on Sep. 12, 2002, herein entirely incorporated by reference and to which the reader is directed for further information.

Optical device 100 utilizes a change in the refractive index upon a surface to determine when a chemically bound material is present within a specific location. For more information concerning colorimetric resonant optical biosensor detection, the reader is referred to "A Plastic Colorimetric Resonant Optical Biosensor for Multiparallel Detection of Label-Free Biochemical Interactions," B. T. Cunningham, B. Lin, J. Qiu, P. Li, J. Pepper, and B. Hugh, *Sensors and Actuators B*, Vol. 85, number 3, November 2002; and "Colorimetric Resonant Reflection as a Direct Biochemical Assay Technique," B. T. Cunnigham, P. Li, B. Lin, and J. Pepper, *Sensors and Actuators B*, Volume 81, p. 316-328, January 2002; the full disclosures of which are herein incorporated by reference.

Figure 2:
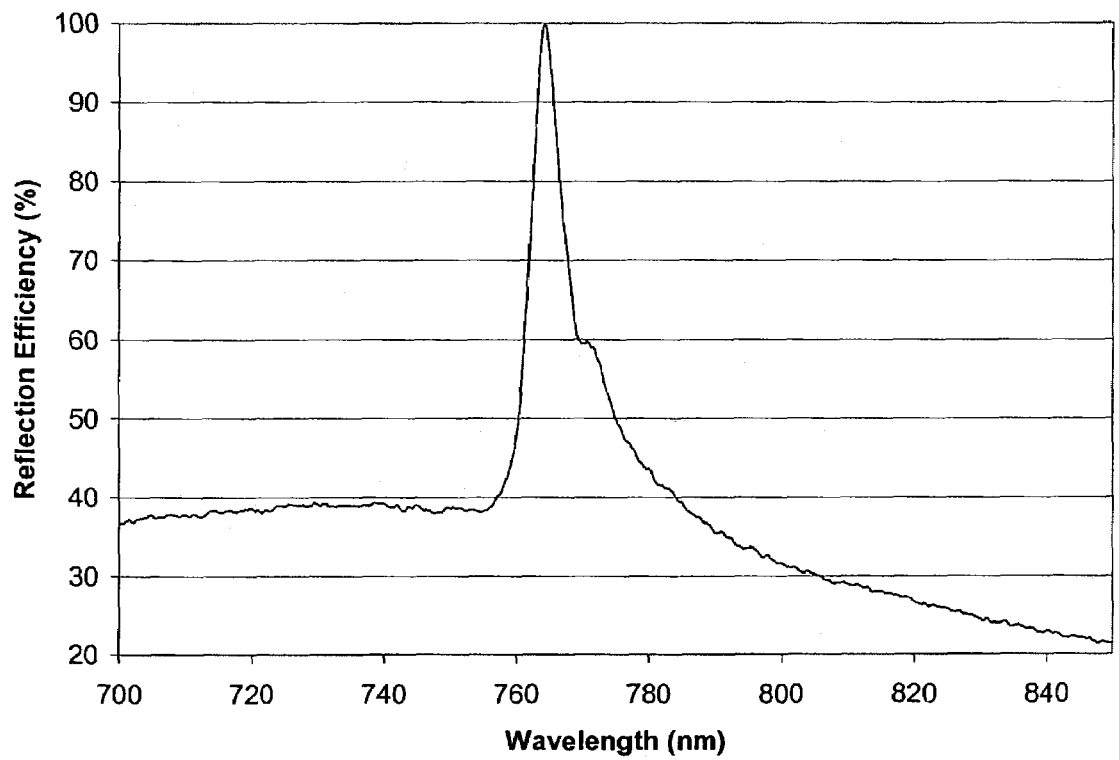
FIG. 2 illustrates an example of measured reflectance spectra of a biosensor by the optical device of FIG. 1.

FIG. 2 illustrates measured reflectance spectra of biosensor 118 of optical device 100 as gathered from spectrometer 116, which records the intensity of gathered light as a function of wavelength. The wavelength measurement range of spectrometer 116 must encompass the resonant wavelength of biosensor 118 to identify biochemical interactions on biosensor 118. For the example illustrated, the resonant wavelength is approximately 765 nm. Therefore, a high intensity of reflected light can be collected at this wavelength.

Measuring apparatus 102 includes a single-point optical spectrometer included in spectrometer 116 to identify biochemical interactions at the resonance wavelength. The spectrometer may be any optical device that is capable of measuring the wavelength as a function of intensity of an incoming light source. Typically, this function is performed by allowing an incoming point light source to reflect against the surface of a diffraction grating. Light of different wavelengths will reflect from the grating surface at different angles to spread the incident point source light according to its wavelength content. Typically, a linear array of optical sensors is positioned to gather the grating-reflected light, where resolvable wavelength illuminates a single element in the optical sensor array. By plotting the output of each optical sensor in the array, and by assigning each optical sensor to a particular wavelength value according to the angle of its reflection of the grating, the intensity as a function of wavelength of the incoming light source may be accurately determined. The resolution of the wavelength determination is a function of the number of optical sensors in the linear array, the distance between the diffraction grating and the sensor array, and the period/depth/accuracy of the diffraction grating.

In the exemplary embodiment, measuring apparatus 102 may include tunable components. For example, spectrometer 116 may be replaced with a narrowband transmission filter whose transmission wavelength can be tuned over the band that encompasses the biosensor resonance wavelength. The tunable filter may be a micro-electro-mechanical (MEM) cantilever containing a Bragg reflector. In addition, in another embodiment, white light source 104 can be replaced with a laser light source (emitting one wavelength at a time) whose wavelength can be tuned over the band that encompasses the biosensor resonance wavelength. For example, the tunable laser may be a vertical cavity surface emitting laser ("VCSEL").

Incorporating tunable components into measuring apparatus 102 allows measuring apparatus to adapt to many types of biosensors to measure biochemical interactions therein. For instance, using spectrometer 116, reflected (or transmitted) light is gathered into spectrometer 116 only when the light is in a range of predetermined (and non-tunable) wavelengths. As such, using a fixed wavelength light source limits operation of measuring apparatus 102 since a high reflected intensity (or low transmitted intensity) is only obtained when a resonance wavelength of the biosensor is within the band of the illuminating radiation form the light source. Therefore, providing a tunable light source and a tunable detector provides for greater flexibility within measuring apparatus 102.

Furthermore, spectrometers are often very expensive, and tend to be bulky. On the other hand, tunable detectors can be designed to be very small (e.g., on the order of 0.1 cm), and can be manufactured at a cost of a fraction of a typical spectrometer.

A tunable light source and a tunable detector may be provided using a number of components. In the exemplary embodiment, the tunable detector and the tunable light source include a VCSEL. A VCSEL is a type of semiconductor diode laser whose emission cavity is perpendicular to the wafer plane. Thus, the VCSEL emits an output optical beam in the vertical direction, with respect to the wafer substrate. A VCSEL cavity may include two distributed Bragg reflectors ("DBRs") with an active region positioned in-between. Typically, the entire cavity is grown in one single-step epitaxy. Subsequent processing is used to create any necessary current and optical confinements. This unique topology also facilitates simple fabrication of arrays and integration of detectors.

Figure 3:
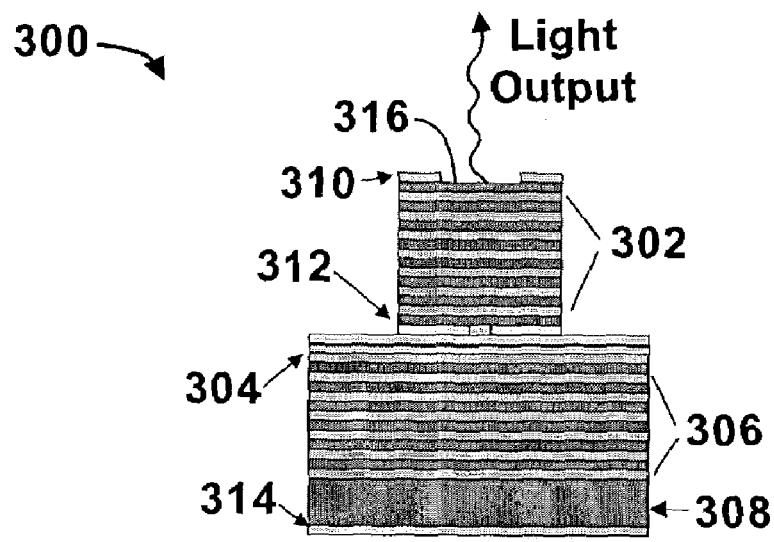
FIG. 3 illustrates one embodiment of a non-tunable diode laser.

FIG. 3 illustrates one embodiment of a non-tunable VCSEL 300. The VCSEL 300 includes a top DBR 302, an active region 304, a bottom DBR 306, and a substrate 308. Top DBR 302 includes contacts 310. Top DBR 302 couples to active region 304 via an oxide confinement 312. In turn, active region 304 directly couples to bottom DBR 306, which also directly couples to substrate 308. Substrate 308 includes a contact 314 positioned on substrate's 308 base. The VCSEL 300 is formed by many layers of heterostructure material grown in the direction normal to substrate 308. VCSEL laser 300 outputs an optical beam from top DBR 302, also in a direction normal to substrate 308.

Top DBR 302 may comprise a p-doped DBR ("p-DBR"), such as an AlGaAs/GaAs lo composition. Likewise, contact 310 may be a p-doped contact. Bottom DBR 306 may comprise an n-doped DBR ("n-DBR"), such as an n-GaAs-Al-GaAs composition. Contact 314, therefore, may be an n-doped contact. Top DBR 302 and bottom DBR 306 comprise alternating layers of semiconductor materials lattice matched to substrate 308, allowing "monolithic" formation of the entire structure during a single epitaxy stage of device fabrication.

VCSEL 300 emits light from a cavity 316 of top DBR 302. VCSEL 300 emits light when a voltage is applied across contacts 310 and 314. The wavelength of the light emitted depends on the amount of voltage applied to the contacts 310 and 314. As one example, for a 1.55 μm wavelength VCSEL, tunable diode laser 300 comprises an active region that is an epitaxial DBR with about 35 layer-pairs of InGaAlAs/In-AlAs, and a bottom DBR 300 comprising a dielectric layer stack as a DBR in conjunction with a gold termination. With an applied voltage drop across contacts 310 and 314 of about 0.9V, VCSEL 300 emits the 1.55 μm wavelength. It should be understood that the VCSEL 300 may contain any number of layers within the top and bottom DBRs, and within the active region, and may also comprise other materials than presented herein to produce other desired wavelengths than described herein. In addition, a VCSEL 300 may be made tunable by many different designs. A few examples include a cantilever VCSEL, a membrane VCSEL, and a half-symmetric cavity VCSEL.

Figure 4:
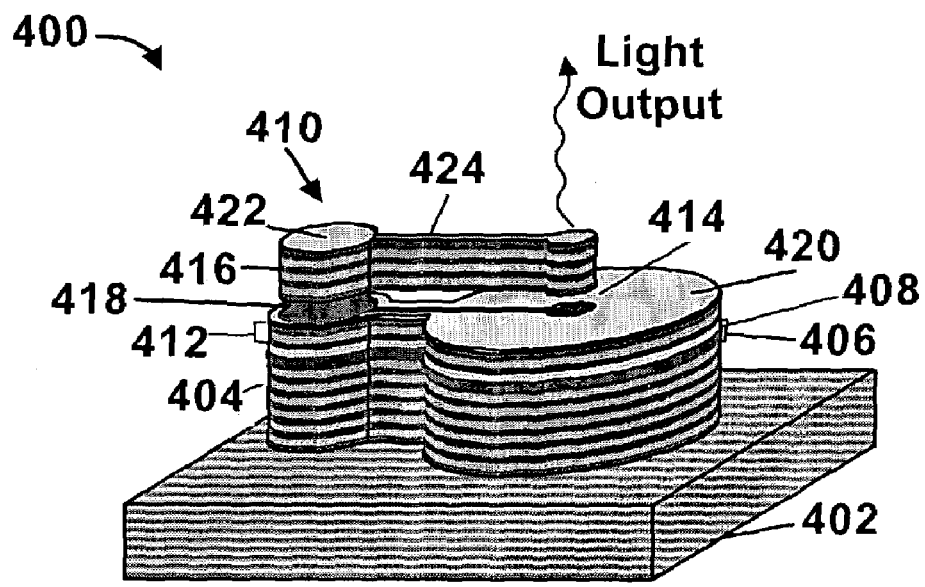
FIG. 4 illustrates one embodiment of a tunable detector with a top mirror positioned on a micro-electro-mechanical structure ("MEMS")

FIG. 4 illustrates an embodiment of a tunable diode laser, such as a tunable VCSEL 400, with a top mirror positioned on a micro-electro-mechanical structure (MEMS). Tunable VCSEL 400 includes a substrate 402, a bottom n-DBR 404, a cavity layer 406 including an active region 408, and a top mirror 410. The top mirror 410 includes a p-DBR 412, an airgap 414, and a top n-DBR 416. Laser drive current is injected through a middle contact 418 via p-DBR 412 and a laser drive contact 420. A tuning contact 422 is fabricated on top n-DBR 416. Wavelength tuning is accomplished by applying voltage between top n-DBR 416 and p-DBR 412, across airgap 414. A reverse bias voltage is used to provide electrostatic force, which attracts a cantilever 424, which is coupled to top n-DBR 416, downward to substrate 402 and shortens airgap 414, thus tuning the laser wavelength toward a shorter wavelength. Thus, tunable VCSEL 400 emits light normal to a surface of cantilever 424 that has a wavelength based on the length of airgap 414.

Since a portion of top mirror 410 suspends above laser drive contact 420, airgap 414 can be adjusted continuously. For example, a continuous tuning range of approximately 32 nm may be achieved with VCSELs centered at a wavelength of 950 nm, with output power greater than 1 mW throughout the tuning range. As tuning is adjusted by applying a voltage to move cantilever 424, the emission speed is limited by the response of cantilever 424, which is typically in the range of microseconds.

In one application, tunable VCSEL 400 may tune over 22 nm continuously and emit a single-mode output with a side mode suppression ratio greater than 45 dB. Tunable VCSEL may transmit at 2.5 giga-bits per second (Gbps) over 100 km single mode fiber. Using similar compound material systems, tunable VCSELs can be made with the center wavelength range from 0.65-1 micron and 1.5-1.6 micron. For more information regarding tunable VCSELs, the reader is referred to C. J. Chang-Hasnain, "Tunable VCSEL," *IEEE Journal of Selected Topics in Quantum Electronics,* 6 (2000), the full disclosure of which is herein incorporated by reference.

The major advantages of VCSELs are low-cost manufacturing and high spectral performance. Testing and packaging constitute a large portion of the manufacturing cost of optoelectronic devices. However, in an equivalent topology with light emitting diodes (LEDs), VCSELs can be tested and packaged in similar low-cost manufacturing processes. For example, large size VCSELs emitting at wavelengths of 850 nm, with a typical dimension of 15-20 micron diameter, can be manufactured in volume at low costs for gigabit Ethernet and other low-cost LAN applications.

Spectral advantages arise because a VCSEL has an ultra short cavity that supports a single Fabry-Perot mode. Thus, a small diameter VCSEL can be made into a single-wavelength single-mode laser. In addition, with a small variation of the cavity thickness, the emission wavelength can tune over a large range.

In one embodiment, tunable VCSEL 400 can be readily translated into a tunable detector or a tunable filter with surface normal topology and array fabrication capabilities. Micromechanically actuated filters can exhibit wide tuning. For example, the tuning range of a MEMS-VCSEL is governed by the wavelength difference resulted from maximum deflection of the cantilever. However, with increases in applied voltage, the cantilevers are pulled onto the substrate, which may result in device damage and reliability issues. A simple analytic approximation of a maximum deflection of the cantilever as well as a capacitive nature of the attractive force is given below in Equation 1.

$$z = \frac{\pi \tau^2 \varepsilon}{E} * \frac{2l^3}{\omega t^3} * \frac{V^2}{(d-z)^2} \qquad \text{Equation 1}$$

Where:
 d airgap size without applied voltage
 z cantilever displacement
 V applied voltage
 E bulk modulus
 $\tau$ radius of the laser
 l length of the cantilever
 $\omega$ width of the cantilever
 t thickness of the cantilever Solving this equation, the maximum deflection of the cantilever, and thus the tuning range, approximates ⅓ of the airgap size. As one example, a wide tuning range of 31.6 nm centered at a wavelength of 950 nm may be achieved with tunable VCSEL 400 operating at room temperature. The tuning voltage to achieve this is about 26V.

FIG. 5A illustrates one embodiment of a tunable detector 500, which may be similar to tunable VCSEL 400. Tunable detector 500 includes a substrate 502, an intrinsic absorption layer 504, a bottom DBR mirror 506, an optical cavity 508, a top DBR mirror 510, an n-contact 512, and a p-contact 514. An air gap 516 is inside top DBR mirror 510. Top DBR mirror 510 is freely suspended by a cantilever 518 with a gap size corresponding to integer multiples of half wavelengths. By applying a voltage (tuning voltage) across top DBR mirror 510 and bottom DBR mirror 506, cantilever 518 is attracted towards bottom DBR mirror 506, and hence airgap 516 size is reduced. More particularly, when a voltage is applied between top DBR mirror 510 and bottom DBR mirror 506, cantilever 518 experiences an electrostatic force pulling cantilever 518 towards substrate 502. The transmission wavelength is therefore tuned.

FIGS. 5B and 5C are schematic diagrams illustrating one embodiment of tuning tunable filter 500. Airgap 516 (thickness L) is designed to pass light that has a desired wavelength (e.g., $\lambda_1$=L) in the non-tuned case. By reverse biasing cantilever 518, top DBR mirror 510 will move towards bottom DBR mirror 506 due to electrostatic forces. The length of airgap 516 is reduced, and consequently shorter wavelengths ($\lambda_2$=L–ΔL) are transmitted through top DBR mirror 510 and bottom DBR mirror 506.

Tunable detector 500 may be a Fabry-Pérot filter, with top and bottom DBR mirrors 510 and 506 forming an optical resonator, and an intrinsic absorption layer under the resonator. Due to multiple reflectances and interferences, only light with a resonant wavelength will be transmitted through tunable filter 500. All other wavelengths are reflected and the multiple reflections cause constructive and destructive interference. By changing the resonator length through deflection of one of the two mirrors, the transmission peaks can be shifted to the wavelength of a desired length.

Top and bottom DBR mirrors 510 and 506 may include Bragg gratings. When a half-wave shift is introduced in an otherwise uniform Bragg grating, the resultant structure behaves as an optical resonator, similar to a Fabry-Perot cavity or a ring resonator. The gratings may be long, uniform structures that perform as wavelength-selective reflectors. Depending upon the characteristics of the Bragg grating, the filter can be configured to perform many different functions. For example, by appropriately selecting the length and depth of the Bragg grating, the reflection spectral response can be made to have a bandpass shape. With this configuration, the device performs as an add/drop filter: one wavelength is transmitted by the gratings, while all other channels are reflected. Another useful device may be realized by making the Bragg grating very shallow, such that peak reflectivity is small.

Figure 6:
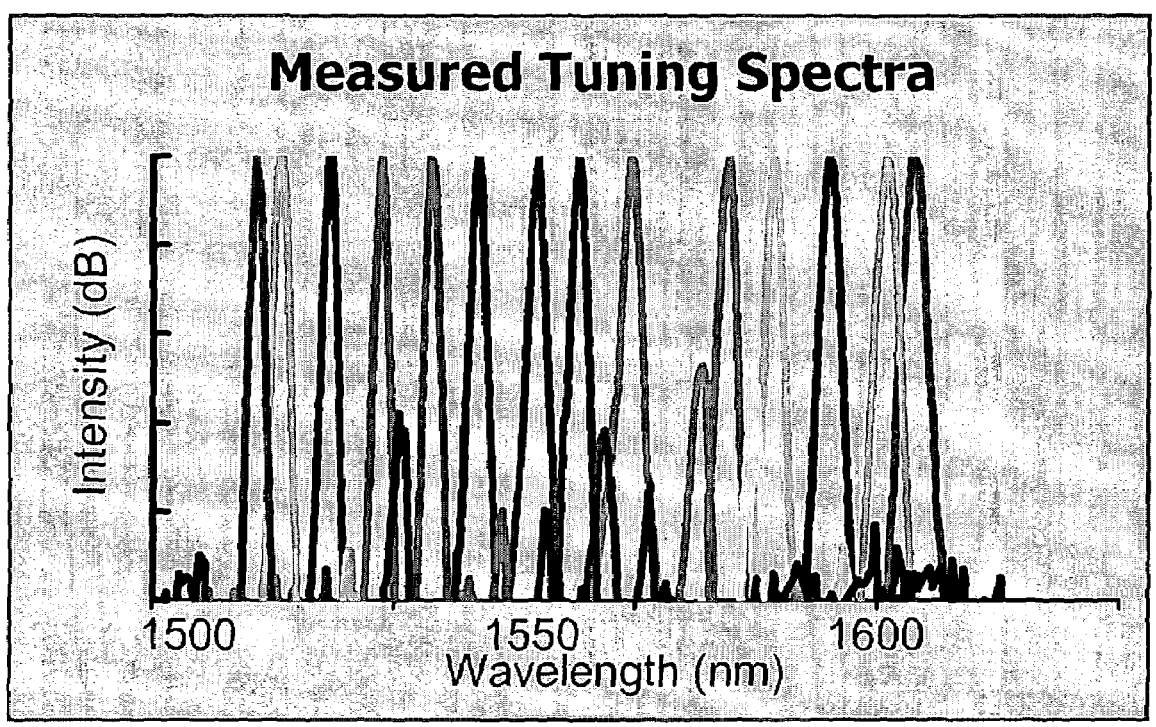
FIG. 6 illustrates one example of a passband spectra of the tunable detector of FIG. 5.

FIG. 6 illustrates spectra of tunable filter 500 passband. The spectra illustrates the wavelength of light transmitted through tunable filter 500 as the tuning voltage is adjusted. As shown, a record of continuous tuning over 100 nm can be achieved. For more information regarding tunable detectors, the reader is referred to Li, G. S.; Yuen, W.; Chang-Hasnain, C. J. "Wide and continuously tunable (30 nm) detector with uniform characteristics over tuning range". *Electronics Letters*, vol.33, (no.13), IEEE, 19 Jun. 1997; and Mateus, C. F. R. et. al., "Widely tunable torsional optical filter", accepted for publication, *IEEE Photonics Technology Letters*, June 2002; the full disclosures of which are herein incorporated by reference.

Figure 7:
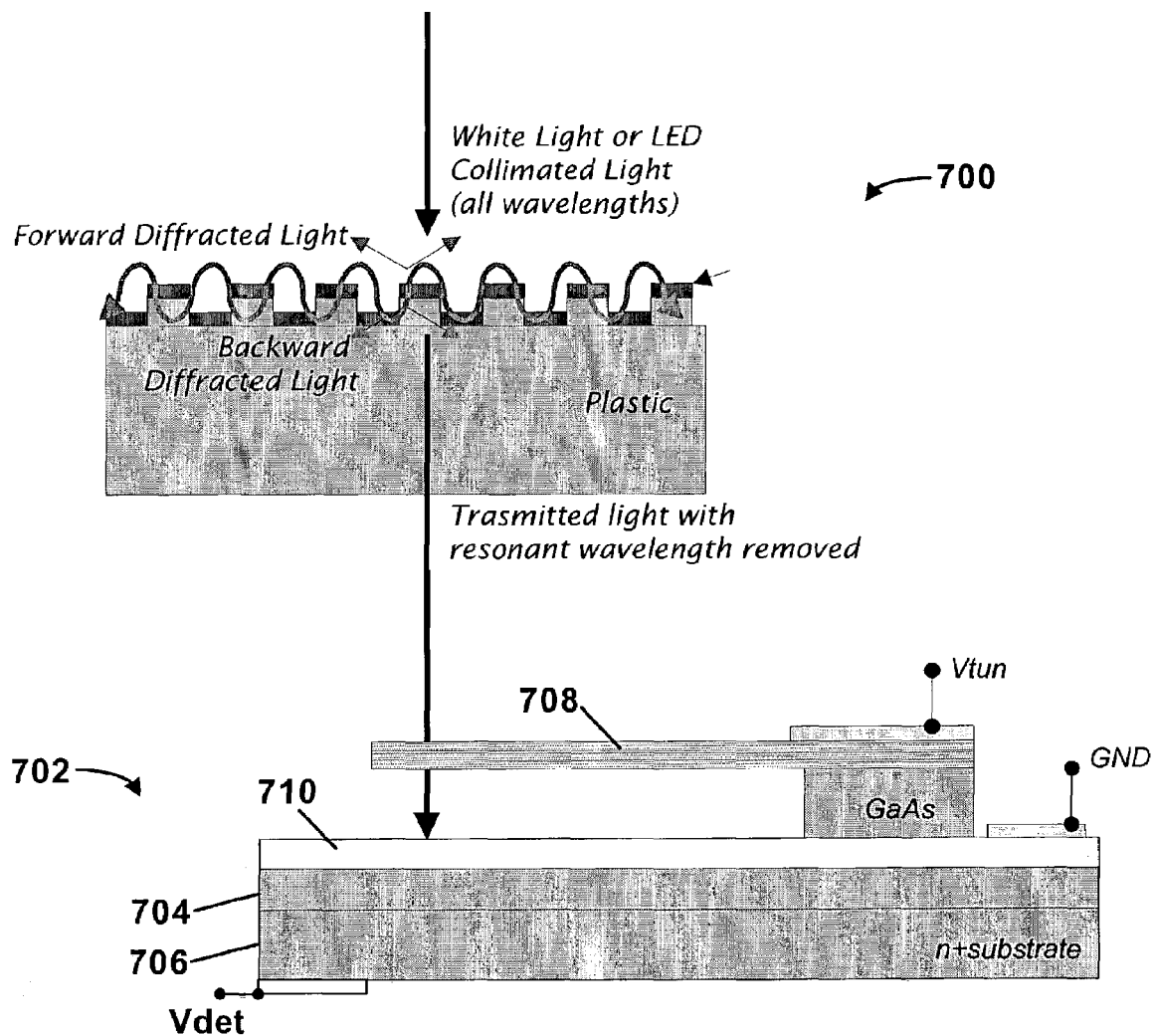
FIG. 7 illustrates one embodiment of colorimetric resonant optical biosensor detection using a tunable filter.

FIG. 7 illustrates one embodiment of calorimetric resonant optical biosensor detection using a tunable detector. FIG. 7 illustrates a biosensor 700 and a tunable detector 702. First, biosensor 700 is illuminated with collimated light at normal incidence from a broadband light source, such as a white light or a light emitting diode ("LED"). The illuminating light interacts with biosensor 700 so that only a narrow band of wavelengths is reflected, while all other wavelengths are transmitted. Biosensor thus produces a peak in reflected intensity as a function of wavelength, and simultaneously produces a minimum in transmitted intensity as a function of wavelength. The wavelength of maximum reflectance and minimum transmittance are identical. Thus, determining the wavelength of minimum transmittance also determines the wavelength of peak reflected intensity (or the PWV).

The light transmitted through biosensor 700 next illuminates an input of tunable detector 702. Tunable detector 702 a tunable filter 704, a photodiode sensor 706, a top DBR 708 and a bottom DBR 710. Tunable filter 704 provides a high degree of light transmission at a narrow band of wavelengths centered at a passband wavelength, $\lambda_f$, but reflects all other wavelengths. The passband wavelength, $\lambda_f$, can be controlled over a range of wavelengths by adjustment of tunable filter's 704 tuning voltage, $V_{tun}$. The passband adjustment range, $\lambda_f(\min)$ to $\lambda_f(\max)$, should encompass a biosensor resonant wavelength, $\lambda_p$. The tuning voltage is continuously adjusted as a function of time, so as to sweep the passband wavelength from $\lambda_f(\min)$ to $\lambda_f(\max)$.

When tunable filter 704 passband does not coincide with the biosensor resonant wavelength, a high intensity of light is transmitted through tunable filter 704. When tunable filter 704 passband does coincide with the biosensor resonant wavelength, a low intensity of light is transmitted through tunable filter 704. A minima in transmitted intensity through tunable filter 704 is obtained at the tuning voltage that produces a passband wavelength that is the same as the resonant wavelength of biosensor 700. To detect the light that is transmitted through tunable filter 704, photodiode sensor 706 is positioned beneath tunable filter 704 as shown in FIG. 7. In the exemplary embodiment, photodiode sensor 706 can be integrated with tunable filter 704. However, photodiode sensor 706 may also be separate from tunable filter 704. Photodiode sensor 706 may be capable of detecting all wavelengths between $\lambda_f(\min)$ and $\lambda_f(\max)$. Photodiode sensor 706 generates an electrical current that is proportional to the intensity of light received. An output of photodiode sensor 706, $V_{det}$, will quantify the amount of light transmitted through tunable filter 704 as a function of the tuning voltage, $V_{tun}$.

Figure 8:
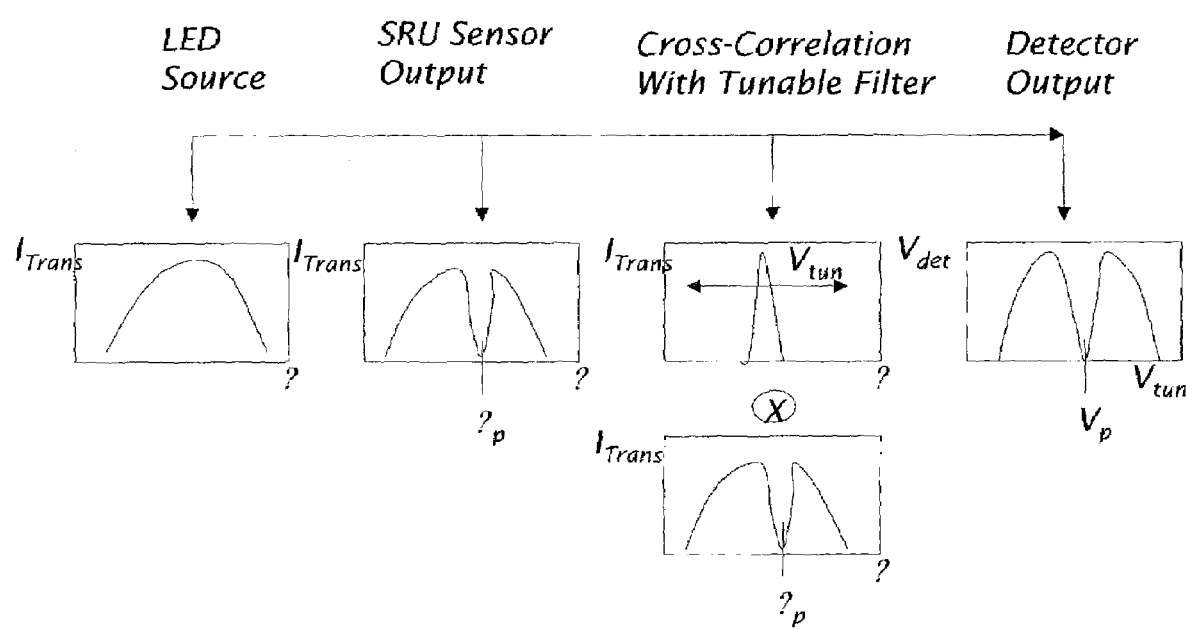
FIG. 8 illustrates one embodiment of a process to obtain a measurement of a biosensor resonant wavelength using a tunable filter.

FIG. 8 illustrates one embodiment of a schematic of a process used to obtain a measurement of the biosensor resonant wavelength using a tunable filter. Initially, a broadband light source produces an illuminating intensity profile as a function of wavelength that encompasses $\lambda_p$. Second, the light passes through biosensor 700, where all wavelengths are transmitted, except the resonant wavelength. Third, the light passes through tunable filter 702, whose wavelength passband is controlled by adjustment of $V_{tun}$. Finally, the light transmitted through tunable filter 702 illuminates photodiode sensor 704, which produces an output voltage $V_{det}$ as a function of $V_{tun}$. A minima in $V_{det}$ is obtained when $V_{tun}$ is adjusted so that $\lambda_f$ coincides with $\lambda_p$.

In an exemplary embodiment, multiple tunable filters can be integrated into a single surface, where each tunable filter is used to measure transmitted light from a different region on a biosensor surface. Each region of the biosensor surface may be activated with a different immobilized molecular receptor (such as different proteins, antibodies, proteins, or DNA). In this manner when the entire biosensor surface is exposed to a test sample, different biosensor regions produce shifts in the resonant wavelength corresponding to the amount of material from the test sample that is gathered onto each individual region. Using any number of microfabrication methods, a linear array of tunable filters, or an x-y grid of identical tunable filters can be produced on a single semiconductor chip.

Figure 9:
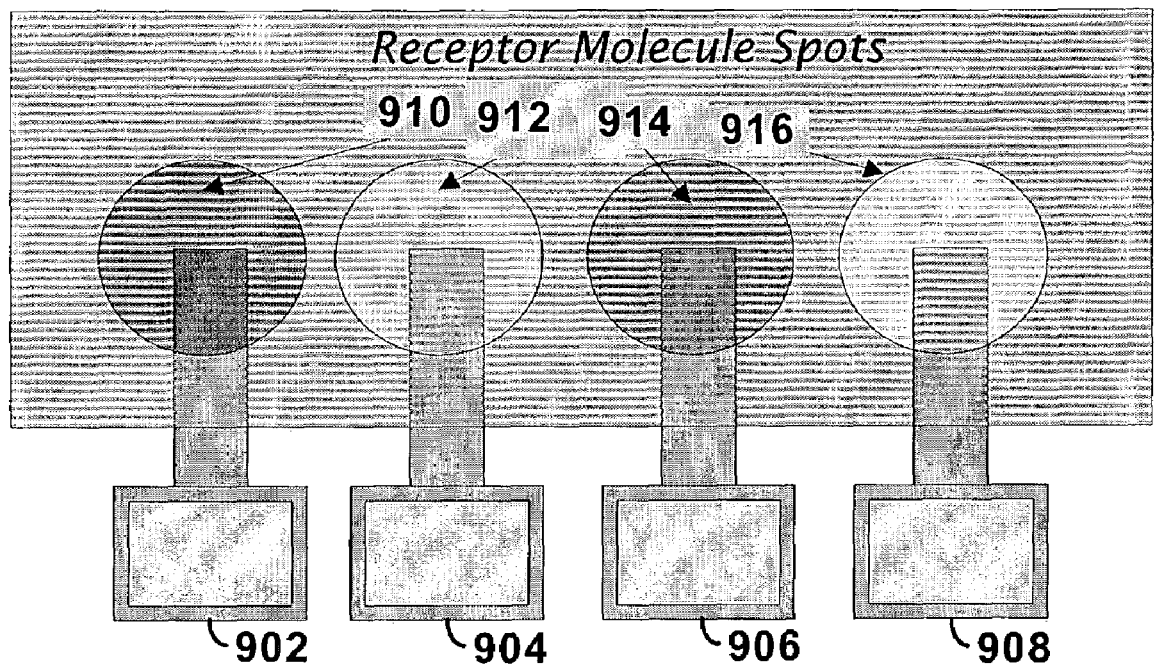
FIG. 9 illustrates a side view of one embodiment of a linear array of tunable filters used to measure separate regions of a biosensor surface.

FIG. 9 illustrates a top view of one embodiment of a linear array of 4 tunable filters 902, 904, 906, and 908 used to measure 4 separate regions of a biosensor surface 910, 912, 914, and 916. In principle, the number of separate filters is limited only by the size of a semiconductor chip, and the density of filter devices. In one embodiment, all the filters in an array may be adjusted simultaneously with a single tuning voltage, while each integrated photodiode sensor has a separate output.

Figure 10:
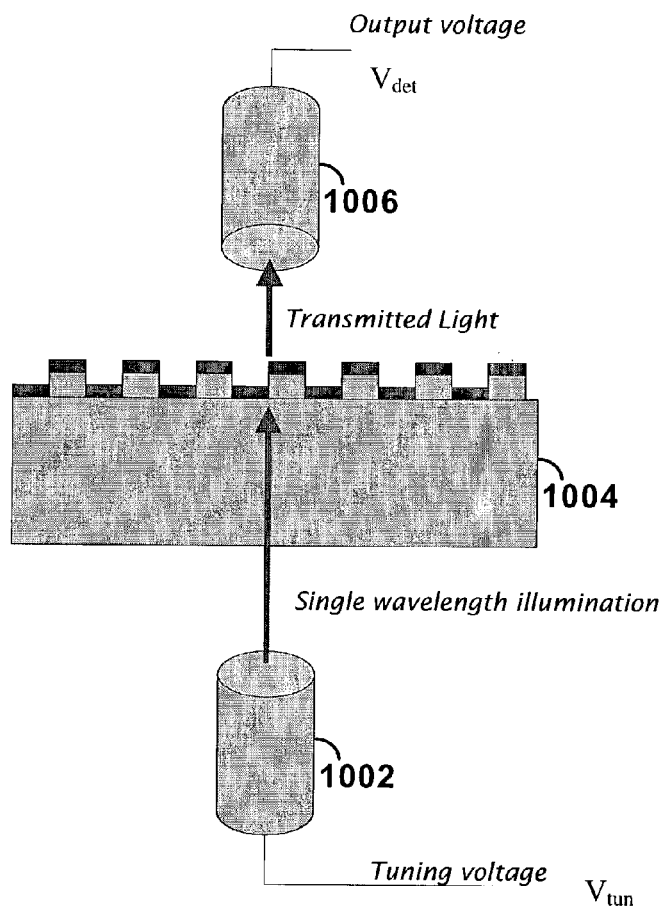
FIG. 10 illustrates another embodiment of a process to obtain a measurement of a biosensor resonant wavelength using a tunable filter.

FIG. 10 illustrates another embodiment of a schematic of a process used to obtain a measurement of the biosensor resonant wavelength using a tunable filter. FIG. 10 illustrates tunable laser 1002, a biosensor 1004, and a photodiode detector 1006. Initially, biosensor 1004 is illuminated at normal incidence by tunable laser 1002. A laser wavelength, $\lambda_{laser}$, is tuned by continuous adjustment of a tuning voltage, $V_{tun}$. The tuning voltage adjusts $\lambda_{laser}$ through a range of wavelengths, $\lambda_{laser}(\min)$ to $\lambda_{laser}(\max)$ that encompasses the sensor resonant wavelength, $\lambda_p$. The illuminating light interacts with biosensor 1004 so that only a narrow band of wavelengths is reflected, while all other wavelengths are transmitted. Biosensor 1004 thus produces a peak in reflected intensity as a function of wavelengths, and simultaneously produces a minimum in transmitted intensity as a function of wavelength. The wavelength of maximum reflectance and minimum transmittance are identical. Thus, determining the wavelength of minimum transmittance also determines the wavelength of peak reflected intensity (or, the PWV). The light transmitted through biosensor 1004 next illuminates photodiode detector 1006 that is capable of detecting a broad band of wavelengths encompassing $\lambda_{laser}(\min)$ to $\lambda_{laser}(\max)$. The output of photodiode 1006, $V_{det}$, will quantify the amount of light transmitted through biosensor 1004 as a function of the laser tuning voltage, $V_{tun}$.

In the exemplary embodiment, tunable laser 1002 is a vertical cavity surface emitting laser (VCSEL) because VCSELs may be fabricated in integrated arrays with many VCSELs on a single semiconductor chip. In one embodiment, multiple VCSELs can be integrated into a single surface, where each tunable VCSEL is used to illuminate a different region on the biosensor surface. Each region of the biosensor surface may activate with a different immobilized molecular receptor (such as different proteins, antibodies, proteins, or DNA), so that when the entire biosensor surface is exposed to a test sample, different biosensor regions produce shifts in the resonant wavelength corresponding to the amount of material from the test sample that is gathered onto each individual region. Using microfabrication methods known in the art, a linear array of tunable VCSELs, or an x-y grid of identical tunable filters can be produced on a single semiconductor chip or assembled onto a surface such as a circuit board.

Figure 11:
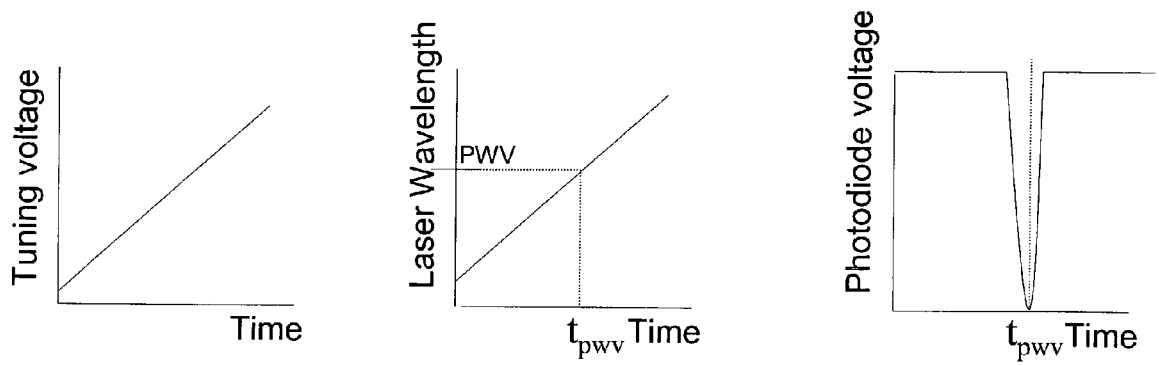
FIG. 11 illustrates one example of tuning voltage output, laser wavelength output and photodiode output with respect to time.

FIG. 11 illustrates one embodiment of the tuning voltage output, laser wavelength output and photodiode outputs with respect to time. As illustrated, as the tuning voltage is increased over time, the laser wavelength output from tunable laser 1002 increases as well. At the time, $t_{pwv}$, when the laser wavelength is at the biosensor resonant wavelength, photodiode 1006 has a minimum in its output.

In the exemplary embodiment, a tunable filter and a tunable laser source are used within calorimetric resonant optical detection. As discussed above, the tunable filter and tunable laser source (e.g., VCSEL), and a pin detector may replace a light source, spectrometer, and a detector array as used in existing implementations (e.g., See FIG. 1).

Figure 12:
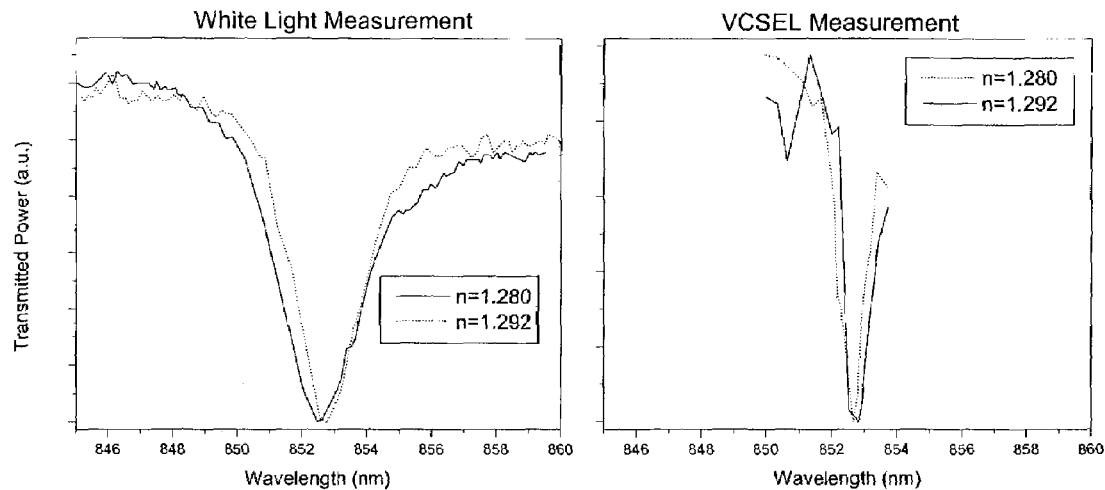
FIG. 12 illustrates one example of reflectance spectra of a tunable filter coated with two index matching fluids for a typical white light measurement and a vertical cavity surface emitting laser ("VCSEL") measurement of a calorimetric resonant optical biosensor.

FIG. 12 illustrates reflectance spectra of a filter coated with two index matching fluids at n=1.280 and n=1.292 for a typical white light measurement and a VCSEL measurement of a colorimetric resonant optical biosensor. As can be seen, the resonant wavelength shifts to longer values with increased index of refraction. The transmission spectra using a VCSEL has a full width at half maximum of 0.4 nm, about ⅓ of that using white light.

As illustrated, biosensor resonance measured with laser excitation produces a more narrow resonant peak than the same biosensor measured by the conventional method (white light illumination and spectrometer detection). The improved behavior may be a result of the more highly collimated and coherent nature of laser light compared to white light. A more narrow resonance can measure small shifts in PWV with finer resolution, thus improving the signal-to-noise ratio for determining shifts in PWV. The higher resolution results in a sensor instrument with the ability to measure lower concentration analytes in test solutions, or smaller molecules with enhanced resolution.

In addition, as described above, the wavelength output of a tunable laser may be continuously adjusted with fine control of the tunable laser's tuning voltage. Wavelength tuning accuracy proportional to the linewidth of the VCSEL may be obtained for such systems. By contrast, spectrometer systems measure the intensity of each wavelength in the spectrum in discrete bins, whose resolution is determined by the period of a reflection grating inside the spectrometer, the size of the spectrometer, and the spatial separation (resolution) of pixels within a linear array of photodiodes that interface to the spectrometer output. For inexpensive spectrometers, the separation between wavelength bins is 0.14 nm, while for large, expensive instruments, the separation between wavelength bins is 0.06 nm. Using these spectrometer instruments, current PWV-shift resolution is approximately 0.001 nm. Therefore, the use of a tunable laser illuminating source can potentially increase PWV detection resolution by an order of magnitude without incurring the cost and size disadvantages of high resolution spectrometer instruments. It is important to note that the resolution advantage may be obtained without making any change to the biosensor.

In the exemplary embodiment, the size of a colorimetric resonant optical biosensor readout instrument based on tunable laser or tunable filter readout can be very small. For tunable VCSEL illumination, a laser power supply and voltage tuning circuit are included. For a tunable filter output, only a low voltage tuning circuit is needed. The tuning circuits can be built using integrated circuit technology to make a biosensor readout interface that is small enough to be handheld. Handheld instruments may be useful in medical diagnostics (such as emergency room or intensive care units), outdoor applications such as environmental monitoring, or placement of self-contained sensor systems within building air ducts.

Figure 13:
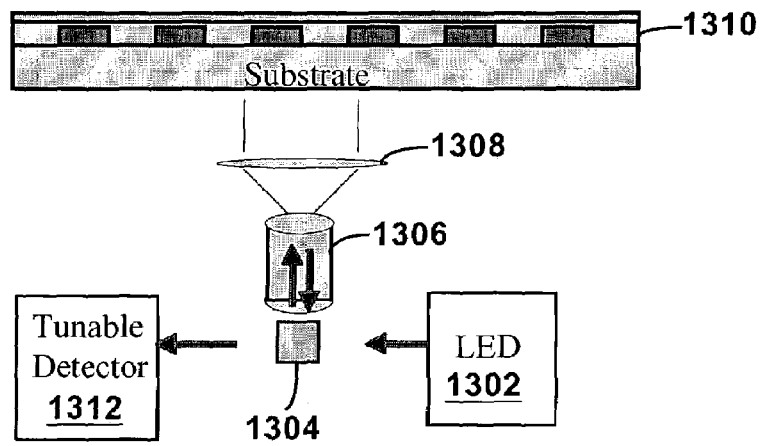
FIG. 13 illustrates one embodiment of a detection configuration using a tunable filter/detector to measure the radiation spectrum reflected from a biosensor.

While the tunable detector detection method described above utilizes detection of a minimum wavelength of transmitted light, the configuration shown in FIG. 13 can be used to detect maximum wavelength of reflected light. FIG. 13 illustrates one embodiment of a detection configuration using tunable filter/detector to measure the radiation spectrum reflected from a biosensor. The configuration includes a LED 1302, a power splitter 1304, an optical fiber probe 1306, a collimation device 1308, a biosensor 1310, and a tunable detector 1312. In this configuration, illuminating broadband light from LED 1302 is coupled into optical fiber probe 1306 through power splitter 1304. The reflected light is gathered by optical fiber probe 1306, and passed to power splitter 1304. Power splitter 1304 sends some of the light to tunable filter/detector 1312. An advantage of this configuration is that alignment of the illumination/detection system is performed through optical fiber probe 1306, rather than by adjustment of the position of the tunable sensor chip.

Figure 14:
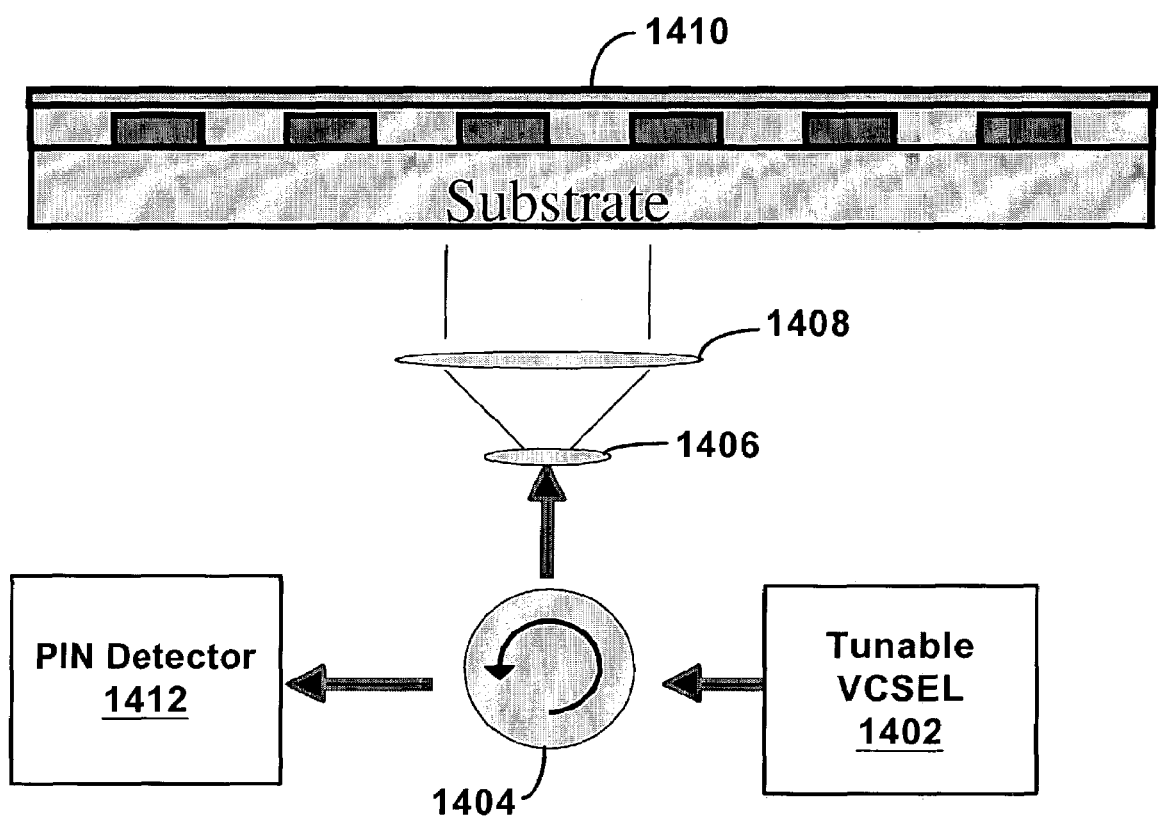
FIG. 14 illustrates one embodiment of a configuration used to detect a maximum wavelength of reflected light.

FIG. 14 illustrates another embodiment of a configuration used to detect a maximum wavelength of reflected light. FIG. 14 illustrates a tunable VCSEL 1402, an optical circulator 1404, a collimation device 1408, a beam expansion device 1406, a biosensor 1410, and a PIN detector 1412. In this configuration, illuminating single wavelength light from tunable VCSEL 1402 is coupled into collimating device 1408 and beam expander 1406 through optical circulator 1410. The reflected light is gathered by collimator 1408 and beam expander 1406, and optical circulator 1410 directs some of the light to PIN detector 1412.

A peak reflecting wavelength can be determined by maximizing PIN detector 1412 signal while varying tunable VCSEL 1402 emission wavelength. As tunable VCSEL 1402 wavelength is tuned, only the wavelength that corresponds to the resonance wavelength of biosensor 1410 resonant will be reflected from biosensor 1410, which performs as a narrow passband reflector. The resolving power, or resolution, of a detector is a measure of how well the detector can distinguish between two slightly different wavelengths. In this case, the resolution will be the laser linewidth. Typical VCSEL linewidth is on the order of 100 MHz, which is about 200 fm at 850 nm.

While exemplary embodiments have been described, persons of skill in the art will appreciate that variations may be made without departure from the scope and spirit of the invention. This true scope and spirit is defined by the appended claims, which may be interpreted in light of the foregoing.

What is claimed is:

1. A measuring apparatus for use in detecting a biochemical interaction, the measuring apparatus comprising, in combination:
   a biosensor, wherein the biosensor comprises a colorimetric resonant optical biosensor embedded into a surface of a device receiving a sample to be tested,
   an illumination system including a light source for generating collimated light, the illumination system and directing the collimated light towards a surface of the biosensor;
   a tunable filter operable to receive light transmitted through the biosensor and to pass a narrow band of light having wavelengths substantially centered at a passband wavelength and to reflect substantially all other wavelength, wherein the passband wavelength is adjusted according to a tuning voltage of the tunable filter, and
   a detector receiving light from the tunable filter wherein the detector of the measuring apparatus detects a biochemical interaction occurring on the colormetric resonant optical biosensor.

2. The invention of claim 1, wherein the tunable filter comprises a micro-electro-mechanical (MEM) cantilever device.

3. The invention of claim 1, wherein the light source comprises a broadband light source.

4. The invention of claim 1, wherein the light source comprises an LED.

5. The invention of claim 1, wherein the light source comprises a tunable laser.

6. The invention of claim 5, wherein the tunable laser comprises a vertical cavity surface emitting laser (VCSEL).

7. The invention of claim 1, wherein the passband wavelength is adjustable over a wavelength range that includes a wavelength at which said biosensor exhibits an optical resonance mode.

8. The invention of claim 1, wherein the tuning voltage is adjusted as a function of time, so as to sweep the passband wavelength.

9. The invention of claim 1, further comprising a photodiode sensor positioned to receive the narrow band of light having wavelengths substantially centered at the passband wavelength from the tunable filter.

10. invention of claim 9, wherein the tunable filter includes the photodiode sensor.

11. invention of claim 9, wherein an output of the photodiode sensor quantifies an amount of the light transmitted through the tunable filter as a function of the tuning voltage of the tunable filter.

12. The invention of claim 1, further comprising a plurality of tunable filters, wherein each tunable filter passes light transmitted through a respective region of the bio sensor.

13. invention of claim 12, wherein the plurality of tunable filters are arranged in a linear array.

14. Apparatus comprising in combination:
a colorimetric resonant optical biosensor embedded in the surface of a device for receiving a sample;
a measuring apparatus for use in detecting a wavelength of maximum intensity in reflected light reflected from the biosensor, the measuring apparatus comprising:
(1) a light source for generating collimated white light;
(2) a power splitter receiving the collimated while light from the light source and directing the collimated white light towards a surface of the biosensor; and
(3) a tunable detector that receives light reflected by the biosensor and measures a radiation spectrum of the light reflected from the biosensor, wherein the tunable detector includes a filter which passes a narrow band of light having wavelengths substantially centered at a passband wavelength from the light reflected by the biosensor, where the passband wavelength is adjusted according to a tuning voltage of the tunable detector;
wherein the tunable detector of the measuring apparatus detects a biochemical interaction occurring on the colorimetric resonant optical biosensor.

15. invention of claim 14, wherein the tunable detector has a micro-electro-mechanical (MEM) cantilever device.

16. The invention of claim 14, wherein the light source comprises a broadband light source.

17. The invention of claim 14, wherein the light source comprises an LED.

18. The invention of claim 14, further comprising an optical fiber probe assembly positioned in an optical path between the power splitter and the biosensor having a first fiber positioned to receive the collimated white light from the power splitter and to direct the collimated white light towards the surface of the biosensor.

19. The invention of claim 18, wherein the optical fiber probe assembly includes a second fiber for receiving the light reflected by the biosensor and directing the light reflected by the biosensor to the tunable detector.

20. The invention of claim 14, further comprising a collimation device positioned to receive the collimated white light from the power splitter and to direct the collimated white light towards the surface of the biosensor.

* * * * *